United States Patent [19]

Kitamura et al.

[11] Patent Number: 5,306,444
[45] Date of Patent: Apr. 26, 1994

[54] WASHING COMPOSITION CAPABLE OF PREVENTING AND AMELIORATING SKIN IRRITATION

[75] Inventors: Kenji Kitamura; Yasukazu Nakayama; Naoe Akiyama; Eriko Kasahara, all of Yokohama, Japan

[73] Assignee: Shiseido Company Ltd., Tokyo, Japan

[21] Appl. No.: 96,206

[22] Filed: Jul. 21, 1993

Related U.S. Application Data

[63] Continuation of Ser. No. 748,230, Aug. 21, 1991, abandoned.

[30] Foreign Application Priority Data

Aug. 24, 1990 [JP] Japan ................... 2-223553
Nov. 1, 1990 [JP] Japan ................... 2-295678

[51] Int. Cl.$^5$ ................................. C11D 3/33
[52] U.S. Cl. ................... 252/546; 252/89.1; 252/156; 252/541; 252/544; 252/547; 252/549; 252/174.16
[58] Field of Search .......... 252/89.1, 156, 541, 252/544, 546, 547, 549, 174.16

[56] References Cited

U.S. PATENT DOCUMENTS

| | | | |
|---|---|---|---|
| 3,658,994 | 4/1972 | Kaiser et al. | 252/DIG. 5 |
| 3,950,509 | 4/1976 | Geks et al. | 252/107 X |
| 4,268,424 | 5/1981 | Hall et al. | 252/DIG. 5 |
| 4,273,684 | 6/1981 | Nagashima et al. | 252/544 |
| 4,313,911 | 2/1982 | Moran et al. | 252/645 X |
| 4,507,233 | 3/1985 | Saito et al. | 252/408.1 X |
| 4,543,333 | 9/1985 | Eilertsen et al. | 252/544 X |
| 4,566,985 | 1/1986 | Bruno et al. | 252/174.12 |
| 4,710,313 | 12/1987 | Miyajima et al. | 252/544 X |
| 4,738,790 | 4/1988 | Miyajima et al. | 252/544 X |
| 4,758,378 | 7/1988 | Raemdonck et al. | 252/544 |
| 4,891,356 | 1/1990 | Szabo | 514/2 |
| 5,053,219 | 10/1991 | Giddey et al. | 252/DIG. 5 |
| 5,071,586 | 12/1991 | Kaiserman et al. | 252/DIG. 12 |

FOREIGN PATENT DOCUMENTS

| | | |
|---|---|---|
| 1939419 | 2/1971 | Fed. Rep. of Germany. |
| 1944568 | 3/1971 | Fed. Rep. of Germany. |
| 2401752 | 7/1974 | Fed. Rep. of Germany. |
| 2016080 | 4/1970 | France. |
| 2216986 | 9/1974 | France. |
| 2457891 | 12/1980 | France. |

OTHER PUBLICATIONS

World Patents Index Latest, AN 85-226613(37), & JP-A-60 146 815, Aug. 2, 1985 (Abstract).
World Patents Index Latest, AN 81-031340 (03) & JP-A-55 145,798, Nov. 14, 1980 (Abstract).
J. Soc. Cosmet. Chem., 35, 183-195 (Jul., 1984).
Arch. Dermatol Res. 281, 45-51 (1989).
Stratum Corneum Water-Holding Properties, 87, No. 6, 758-761 (1986).
The Journal of Investigative Dermatology, 93, No. 5, 695-699 (1989).
J. Soc. Cosmet. Chem. Japan, 19, No. 1, S84-S94 (1985) English Abstract.

*Primary Examiner*—Patrick P. Garvin
*Attorney, Agent, or Firm*—Sprung, Horn, Kramer & Woods

[57] ABSTRACT

A washing composition for a domestic or business detergent and a skin cleanser containing one or more compounds having a protease inhibitory activity.

3 Claims, No Drawings

WASHING COMPOSITION CAPABLE OF PREVENTING AND AMELIORATING SKIN IRRITATION

This application is a continuation of application Ser. No. 07/748,230, filed Aug. 21, 1991, now abandoned.

BACKGROUND OF THE INVENTION

1. Field of the Invention

The present invention relates to a novel washing agent. More specifically, it relates to a detergent composition for domestic or business use or a skin cleanser composition comprising one compound or two or more compounds selected from compounds having a protease inhibitory activity, which prevents and ameliorates skin irritation, and at the same time, is harmless to the human body and has a strong washing power.

2. Description of the Related Art

Washing compositions such as cleansers and detergents have been generally employed for removing contaminates or soils attached to the surface or internally of materials and the human body, and may be broadly classified into 1) those used for the human body, 2) those used for clothing and fiber products, 3) and those for washing soft and rigid surfaces.

Among these cleansers, the cleanser for the human body (i.e., skin) is intended to remove the fat and sweat secreted from the skin surface, and other corneum cells detached as a result of metabolism (i.e., dirt), outside contamination attached thereto, and cosmetics.

The surfactant contained in a detergent is a chemical exhibiting a washing power and foaming power which are inherent properties of the detergent, but these are known to have an adverse influence on human skin. A detergent which comes directly into contact with human skin must produce only a weak irritation of the skin or eyes.

For skin cleansers, surfactants with a low irritation effect have been developed to obtain useful products, but there remains a need to improve the washing power and foaming power thereof.

For the washing of the human body, surfactants with a low irritation, effect have been developed to obtain useful products, but there remains a need to improve the washing power and foaming power, and a product which fully satisfies users has not yet been developed. Further, even though the composition has a low irritation effect, it would be more useful if a chemical which treats and ameliorates skin irritation were formulated therein.

On the other hand, currently, for washing objects other than the human body, the surfactants primarily used have a strong washing power but also cause an irritation of the skin or eyes. Although efforts to improve safety have been made by working with the use of protective tools such as gloves, or by way of aftercare after completion of the work, the sensitivity of the fingertips may be lost depending the work, and thus the wearing of gloves may be unsuitable in some cases; sometimes skin irritation is reported to be generated by the gloves per se. Also, although the practice of aftercare after the completion of work is is important, it is considered more useful if the chemical acts during the work.

Many proteases are known to exist, which maintain the structure and constancy of the skin functions, and the important role thereof thus recently attracted more attention. A protease or proteolytic enzyme is the comprehensive name for enzymes which catalyze a peptide bond by hydrolysis, and such proteases are classified into peptidases and proteinases. The former are enzymes which cleave the peptide bond from the outside of the amino group terminal end or the carboxyl group terminal end of a protein or a peptide chain, and the latter proteinase are enzymes which cleave the specific bond internally of a peptide chain. Such proteinases are known as "protease" in a broad sense, and further, are broadly classified, according to the properties of their active sites, into 1) serine type, 2) thiol (cysteine) type, 3) carboxyl type and 4) metal proteinase, and specific inhibitors exist for the respective enzymes.

SUMMARY OF THE INVENTION

The objects of the present invention are to obviate the above-mentioned problems of the prior art and to provide a washing composition containing one or more compounds having a protease inhibitory activity, which prevents and ameliorates skin irritation, and is harmless to the human body and has a strong washing power.

Other objects and advantages of the present invention will be apparent from the following description.

In accordance with the present invention, there is provided a washing composition comprising at least one compound having a protease inhibitory activity and dermatologically acceptable components for a conventional washing composition.

DESCRIPTION OF THE PREFERRED EMBODIMENTS

The present inventors, in view of the state of the art as described above, have made an intensive study of the relationship between various chemicals and skin irritation treatment and amelioration, for treating and ameliorating skin irritation by formulating an effective chemical in the detergent itself, which has not been practiced in the prior art, and consequently, found that a washing composition formulated with a protease inhibitor provides an excellent amelioration of skin irritation, and accomplished the present invention based on thus finding.

The constitution of the present invention is now described as follows.

More specifically, the first aspect of the present invention concerns a detergent for domestic or business use, comprising one or two or more compounds selected from compounds having a protease inhibitory activity.

The detergent composition for domestic or business use of the present invention includes washing detergents for domestic use, washing detergents for business use (laundry detergents, dry cleaning detergents), washing aids (softeners, bleaching agents, glue agents, water repellents), stain remover, carpet shampoo, rust remover, detergents for kitchen (for vegetables, fruits, dish, cooking tools, etc.), oven cleaner, floor polish, floor wax, floor cleaner, floor wax remover, stain remover of floor, window glass detergent, blind cleaner, toilet stool detergent, porcelain detergent, marble detergent, stone wall detergent, wall paper detergent, wall paper and label peeling agent, paint face detergent, paint peeling agent, plastic cleaner, metal face detergent, furniture polisher, slippery agent of door, paper screen, automobile body detergent, car polish, automobile part detergent (type cleaner, inner engine carbon remover, radiator cleaner, mechanical part detergent electrical insulator detergent, brake lining cleaner, etc.), aerocraft detergent, metal detergent (iron, copper and general metal detergent, stainless steel and chromium face detergent, aluminum detergent copper and copper alloy detergent silver detergent, etc.), detergents for press for printing, rolls ink bottle, etc., detergents for dairy industries, tank detergents, discharge pipe, sewage reservoir detergent, leather product detergent, she cleaner, shoe polish, spectacle lens cleaner, artificial tooth cleaner, refrigerator detergent, deodorant, road detergent, etc.

The second aspect of the present invention concerns a skin cleanser composition comprising one or two or more compounds selected from compounds having a protease inhibitory activity.

The skin cleanser composition of the present invention is intended to remove various contaminates attached to the human body, and from animals such as pets and domestic stock.

Specifically, the following compositions may be included in the second aspect of the present invention, but it is not limited thereto.

The compositions include soap, hand cleansers, body shampoos, body lotions, pre-shaving lotions, shaving foams, cleansing creams, cleansing lotions, and pet shampoos.

A protease or proteolytic enzyme is the comprehensive name for enzymes which catalyze a peptide bond by hydrolysis, and such proteases are classified into peptidases and proteinases. The former are enzymes which cleave the peptide bond from the outside of the amino group terminal end or the carboxyl group terminal end of a protein or a peptide chain, and the latter proteinase are enzymes which cleave the specific bond internally of a peptide chain. Such proteinases are known as "protease", in a broad sense, and further, are broadly classified, according to the properties of their active sites, into 1) serine type, 2) thiol (cysteine) type, 3) carboxyl type and 4) metal proteinase, and specific inhibitors exist for the respective enzymes.

The protease inhibitor or the compound having a protease inhibitory activity usable in the present invention includes all the chemical substances capable of inhibiting, reversibly or irreversibly, the hydrolysis activity of the above protease or proteolytic enzyme.

Specifically, the following substances are included.

(1) Compounds derived from animals or vegetables: preferably a bovine pancreatic basic trypsin inhibitor, aprotinin, soybean trypsin inhibitor, rimabean protease inhibitor, and corn protease inhibitor.

(2) Compounds derived from microorganisms: preferably antipine, plasminostreptin, and further, compounds comprehensively known as leupeptin and represented by the following formula:

$$R_1-R_2-R_3-NH-\underset{CHO}{\underset{|}{CH}}-(CH_2)_3-NH-\underset{+NH_2}{\overset{\|}{C}}-NH_2$$

$R_1$ = CH$_3$CO, CH$_3$CH$_2$CO
$R_2$ = L-Leu, L-Ile, L-Val
$R_3$ = L-Leu, L-Ile, L-Val
(Leu: leucine, Ile: isoleucine, Val: valine)

(3) Benzamidine and derivatives thereof: preferably benzamidine, p-aminobenzamidine, m-aminobenzamidine, phenylguanodine, (2R,4R)-4-methyl-1-[N$^2$-(3-methyl-1,2,3,4-tetrahydro-8-quinolinesulfonyl)-L-arginyl]-2-piperidinecarboxylic acid monohydrate, and duncylarginine N-(3-ethyl-1,5-pentanedyl)amide.

(4) Acetamide and derivatives thereof: preferably acetamide and 2-phenylacetamide, cyclohexylacetamide.

(5) Guanidine and derivatives thereof: preferably phenylguanidine and cyclohexylguanidine.

(6) ω-amino acids:
Preferably tranexamic acid, p-aminomethylbenzoic acid, 4-aminomethylbicyclo(2,2,2)octane-1-carboxylic acid, 5-[trans-4(aminomethyl)cyclohexyl]-tetrazole, 3-[trans-4(aminomethyl)cyclohexyl-2-oxopropionate, trans-4-(aminomethyl)cyclohexyl glyoxal monohydrate, and trans-4-(aminomethyl)cyclohexane hydroxamic acid, or substances represented by the following formula wherein the carbon chain has n = 1−8

$$NH_2(CH_2)_nCOOH.$$

The present invention is not limited to the above, but among these ω-amino acids, particularly good effects can be recognized in ε-aminocaproic acid and tranexamic acid, and in p-aminomethylbenzoic acid.

(7) Fluorophosphoric acid and derivatives thereof: preferably diisopropylfluorophosphoric acid.

(8) Fluorosulfonic acid and derivatives thereof: preferably phenylmethanesulfonyl fluoride, and [(p-amidinophenyl)methanesulfonyl fluoride.

(9) Guanidinobenzoic acid and derivatives thereof:
Preferably p-nitrophenyl-p'-guanidinobenzoic acid, 3',6'-bis(4-guanidinobenzoyloxy)-5-(N'-4-carboxyphenyl)thioureidospiro[isobenzofuran-1(3H), and 9'-(9H)xanzene]-3-one.

(10) Lysine and derivatives thereof: preferably compounds represented by the following formula:

$$R_1-NH-(CH_2)_4-\underset{\underset{R_3}{\underset{|}{NH}}}{\underset{|}{CH}}-CO-R_2$$

$R_1$ = H, Phe-Ala, Ala-Phe
$R_2$ = OH, CH$_2$Cl
$R_3$ = H, $$SO_2-\underset{}{\underset{}{\bigcirc}}-CH_3$$

(Phe: phenylalanine, Ala: alanine)

The present invention is not limited to the above, but among these lysine and derivatives thereof, a particular good effect is recognized in $R_2$ = CH$_2$Cl.

(11) Arginine and derivatives thereof: preferably the compounds represented by the following formula:

$$R_1-NH-\underset{+NH_2}{\overset{\|}{C}}-(CH_2)_3-\underset{\underset{R_3}{\underset{|}{NH}}}{\underset{|}{CH}}-CO-R_2$$

$R_1$ = H, D-Phe-Pro, Glu-Gly, Ile-Glu-Gly, Pro-Phe, Ala-Phe $R_2 = OH, CH_2Cl$
$R_3 = H,$

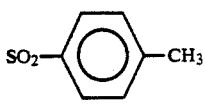

(Phe: phenylalanine, Pro: proline, Glu: glutamic acid, Gly: glycine, Ile: isoleucine, Ala: alanine)

The present invention is not limited to the above, but among these arginind and derivatives thereof, a particularly good effect is recognized in $R_2 = CH_2Cl$.

The respective substances as mentioned above have been known only to have protease inhibitory activities, and have not been known to prevent and ameliorate skin irritation.

In the present invention, the compounds having a protease inhibitory activity as mentioned above can be used alone or in any combination thereof.

Also, in the present invention, the amount of the compound having a protease inhibitory activity and formulated in the washing composition is preferably 0.0001 to 20% by weight, more preferably 0.001 to 5% by weight. If less than 0.0001% by weight, the effect of the present invention is not obtained, and an amount over 20% by weight is not preferable from the standpoint of preparation and cost.

The "skin irritation treatment and amelioration effect" as mentioned in the present invention means the activity as shown below.

Specifically, this term refers to an amelioration of the disappearance or obscuration of the peeling of the corneum, skin grooving and skin swelling due to the use of the cleaners of the prior art.

In the washing composition of the present invention, in addition to the compounds having a protease inhibitory activity, there can be formulated, if necessary, pharmaceutically or dermatologically acceptable surfactants (anionic, cationic, nonionic, amphoteric, semipolar) aids (builder), abrasives, fluorescent brightness, bleaching agents, colorants, preservatives, sequestering agents, antistatic agents, precipitation preventives, antioxidants, perfumes, oils, humectants, and chemicals such as antiphlogistic agents, sterilizers, and vitamins within the range which does not impair the effect of the present invention.

As examples of the above-mentioned additives, the anionic surfactants include:

i) fatty acid soap type anionic surfactants represented by the formula:

RCOOM (wherein R represent an alkyl group or alkenyl group having 8 to 18 carbon atoms, M represents one or two or more of alkali metals, organic amines, and basic amino acids);

ii) ether carboxylic acid salt type anionic surfactants represented by the formula:

$R(OCH_2CH_2)_nOCH_2COOM$ (wherein R represents an alkyl group or alkylallyl group having 8 to 22 carbon atoms, n is an integer of 1 to 16, and M represents one or two or more of alkali metals, organic amines, and basic amino acids);

iii) N-acylsarcosine salt type anionic surfactants represented by the formula:

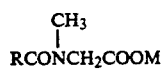

(wherein R represent an alkyl group or alkenyl group having 8 to 18 carbon atoms, and M represents one or two or more of alkali metals, organic amines, and basic amino acids);

iv) anionic surfactants having a

in the formula represented by condensed products of higher fatty acids and amino acids such as N-acylglutamic acid salts represented by the formula:

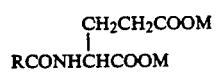

(wherein R represents an alkyl group or alkenyl group having 8 to 18 carbon atoms, and M represents one or two or more of alkali metals, organic amines, and basic amino acids).

More specifically, anionic surfactants can include base materials for soap; fatty acid soaps such as sodium laurate, sodium palmitate or the like; higher alkyl sulfate salts such as sodium lauryl sulfate, potassium lauryl sulfate or the like; alkyl ether sulfate salts such as triethanolamine polyoxyethylene (hereinafter abbreviated as POE) lauryl sulfate, sodium POE lauryl sulfate or the like; N-acylsarcosine such as sodium lauroylsarcosinate or the like; higher fatty acid amide sulfonic acid salts such as sodium N-myristoyl-N-methyltaurine, sodium coconut oil fatty acid methyltauride, sodium lauryl methyltauride or the like; phosphate salts such as sodium POE oleyl ether phosphate, and POE stearyl ether phosphoric acid or the like; alkylhydroxycarboxylic acid salts such as sodium laurylhydroxy ether carboxylate or the like; sulfosuccinic acid salts such as sodium di-2-ethylhexylsulfosuccinate, sodium monolauroyl monoethanolamide polyoxyethylene sulfosuccinate, and sodium lauryl polypropylene glycol sulfosuccinate or the like; alkylbenzene sulfonic acid salts such as sodium linear dodecylbenzene sulfonate, triethanolamine linear dodecylbenzene sulfonate, and linear dodecylbenzene sulfonic acid or the like; N-acylglutamate salts such as monosodium N-lauroylglutamate, disodium N-stearoylglutamate, and monosodium N-myristoyl-L-glutamate or the like; higher fatty acid ester sulfuric acid salts such as sodium hardened coconut oil fatty acid glycerine sulfate or the like; sulfated oil such as Turkey red oil; POE alkyl ether carboxylic acids, POE alkylallyl ether carboxylic acid salts, α-olefinsulfonic acid salts, higher fatty acid ester sulfonic acid salts, secondary alcohol sulfonate salts, higher fatty acid alkylolamide sulfate salts, sodium lauroyl monoethanolamide succinate, di-triethanolamine N-palmitoylaspartate, and sodium caseinate, and so on.

The cationic surfactants include monoalkyl type quaternary ammoniums salts represented by the formula:

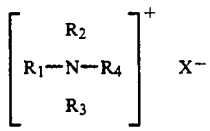

(wherein $R_1$ represents an alkyl group or alkenyl group having 12 to 22 carbon atoms, $R_2$, $R_3$ and $R_4$ represent methyl or ethyl group, X represents a halogen atom or a methyl sulfate residue), and further, aliphatic amine salts, aromatic quaternary ammonium salts, pyridinium salts, and imidazolinium salts.

The nonionic surfactants can include glycerine fatty acid esters, sorbitane fatty acid esters sorbitol fatty acid esters, sucrose fatty acid esters, polyoxyethylene (hereinafter called POE) sorbitane fatty acid ester, polyoxyethylene glycol fatty acid esters, POE alkyl ethers, POE alkylphenyl ethers, POE hardened castor oil derivatives, mannitol hydroxyfatty acid ethers, and alkylglycoside fatty ethers.

The amphoteric surfactants can include carboxybetaines such as N,N-dimethyllauryl-N-carboxymethylammonium betaine, N,N-dimethyl-N-oleyl-N-carboxymethylammonium betaine, and lauryldimethylaminoacetic acid or the like; imidazoline derivatives such as 2-lauryl-N-carboxyethyl-N-hydroxyethylimidazolinium betaine, 2-lauryl-N-carboxymethyl-N hydroxyethylimidazolinium betaine, 2-undecyl-N,N,N-(hydroxyethylcarboxymethyl)-2-imidazoline sodium, and 2-cocoyl-2-imidazolilinium hydroxide-1-carboxyethyloxy-2-sodium or the like; aminocarboxylic acid salts such as sodium N-coconutalkyl-$\beta$-aminopropionate and sodium N-coconutalkyl-$\beta$-iminodipropionate or the like, and sulfobetaine and aminobetaine.

The semi-polar surfactants can include lauryldimethylamine oxide, stearyldimethylamine oxide, and bis-(2-hydroxyethyl)lauryl-amine oxide.

As the propellant, all propellants which can be used in aerosol products in general are applicable. Specifically, there include fluorinated hydrocarbons such as Freon 11 (registered trade mark) Freon 12 (registered trade mark), Freon 21 (registered trade mark), Freon 113 (registered trade mark), and Freon 114 (registered trade mark), liquefied petroleum gas (L. P. G.) which is a mixture of propane, isobutane, n-butane, and a compressed gas such as carbon dioxide gas and nitrogen gas. These gases can be used either alone or as a mixture of two or more kinds thereof, and the amount formulated is generally 2 to 20% by weight. With an amount of 2% or less, the internal pressure may be lower, and thus the stock liquid may not be properly emitted upon use, and on the other hand, further improved results cannot be obtained if 20% or more of the gas is employed; conversely, the internal pressure may become too high.

Any conventionally used water-insoluble oil may be employed, for example, higher alcohols such as cetyl alcohol, stearyl alcohol, and cholesterol or the like; higher fatty acids having $C_8$-$C_{22}$ carbon atoms such as lauric acid, myristic acid, palmitic acid, stearic acid, oleic acid, and isostearic acid or the like; waxes such as solid paraffin, microcrystalline wax, polyethylene wax, canderilla wax, beeswax, hardened castor oil, carunauba was, and barico wax or the like; animals and vegetable oils such as tallow, lard, sheep oil, squalane, coconut oil, palm oil, palmkernel oil, soybean oil, olive oil, cottonseed oil, jojoba oil, castor oil, and lanolin; mineral oils such as fluid paraffin and petrolatum; and synthetic oils such as trimethylpropane triisostearate, isopropyl myristate, glycerol tri-2-ethylhexanate, pentaerythritol tetra-2-ethylhexanate, silicone oil, and polyoxyethylene polyoxypropylene pentaerythritol ether.

Any conventionally used polyhydric alcohol may be employed, for example, propylene glycol, dipropylene glycol, glycerine, 1,3-butylene glycol, polyethylene glycol, polyoxyethylene methylglycoside ether, polyoxyalkylene diglyceryl ether, polyoxyalkylene polyglyceryl ether, polyoxyalkylene decaglyceryl ether, polyoxyalkylene pentaerythritol ether, sorbitol, maltitol, lactose, and D-mannitol.

Further, there can be included sterilizers such as cetylpyridinium chloride, benzetonium chloride, decalinium chloride, benzalkonium chloride, chlorohexydine gluconate, carbanilide, phenol, and halogenated salicylanilide, alkalis such as caustic potash and ammonia, lower alcohol such as ethanol, and humectants such as mucopolysaccharides and pyrrolidone carboxylic acid salts, etc. Other humectants are propylene glycol, dipropylene glycol, glycerine, 1,3-butylene glycol, polyethylene glycol, polyoxyethylene methylglycoside ether, polyoxyalkylene diglyceryl ether, polyoxyalkylene polyglyceryl ether, polyoxyalkylene decaglyceryl ether, polyoxyalkylene pentaerythritol ether, sorbitol, maltitol, lactose, D-mannitol, mucopolysaccharide, and pyrrolidone carboxylic acid salts.

The abrasives usable in the detergent composition for domestic or business use include silicates such as sodium metasilicate or the like, salts such as sodium sulfate and sodium carbonate, silica, borax, talc, diatomaceous earth, bentonite, colloidal clay, fluorite, quartz, and sand.

The washing composition according to the present invention may be in any desired form, as long as it is in the form suitable for accomplishing the object of providing a detergent, as exemplified by a liquid (lotion, milky lotion), cream, solid, fine granules, and powder.

The washing composition of the present invention can be used while washing, and prevents and ameliorates skin irritation, and at the same time, is harmless to the human body and has a strong washing power.

EXAMPLES

The present invention will now be further illustrated by, but is by no means limited to, the following Examples and Actual Use Examples.

Prior to the Examples, the test methods and evaluation methods practiced for clarifying the prevention of skin irritation and amelioration of skin irritation effects of the compound having a protease inhibitory activity according to the present invention are explained.

Actual Use Test I-1

Sixty housewives 40 to 60 years old and susceptible to "skin irritation" when continuously using conventional synthetic detergents in the kitchen were selected as the subjects to be tested and divided into 6 groups each having 10 members. For the subjects to be tested of 5 groups, the respective Examples shown in Table I-1 were used, and for the subjects to be tested of the remaining one group, Comparative Example I-1 was used. Continuous use tests were conducted for 4 weeks, and thereafter, the state of the skin of the back of the hands was observed by the replica method, and evaluated according to the judgement standards shown in Table I-2. Each recipe was prepared according to conventional methods, to obtain a synthetic detergent for kitchen.

TABLE I-1

|  | Example | | | | | Comparative Example |
|---|---|---|---|---|---|---|
|  | I-1 | I-2 | I-3 | I-4 | I-5 | I-1 |
| Sodium POE (3 mole) alkyl ether sulfate | 15.0 | 15.0 | 15.0 | 15.0 | 15.0 | 15.0 |
| POE (15 mole) alkyl ether | 5.0 | 5.0 | 5.0 | 5.0 | 5.0 | 5.0 |
| Coconut fatty acid ethanol amide | 6.0 | 6.0 | 6.0 | 6.0 | 6.0 | 6.0 |
| Ethanol | 1.0 | 1.0 | 1.0 | 1.0 | 1.0 | 1.0 |
| Perfume | q.s. | q.s. | q.s. | q.s. | q.s. | q.s. |
| Dye | q.s. | q.s. | q.s. | q.s. | q.s. | q.s. |
| Purified water | balance | balance | balance | balance | balance | balance |
| Tranexamic acid | 1.0 | — | — | — | — | — |
| Leupeptin | — | 0.5 | — | — | — | — |
| Tosylarginine | — | — | 3.0 | — | — | — |
| Tosyllysyl chlormethyl ketone | — | — | — | 0.05 | — | — |
| Soybean trypsin inhibitor | — | — | — | — | 0.1 | — |

TABLE I-2

| Score | Evaluation | Remarks |
|---|---|---|
| 1 | Disappearance of skin groove, skin rise Peeling of wide range of corneum | Irritated skin ↑ |
| 2 | Obscure skin groove, skin rise Partial peeling of corneum | ↑ |
| 3 | Skin groove, skin rise recognized, but flat | ↓ |
| 4 | Clear skin groove, skin rise | ↓ |
| 5 | Skin rise, skin groove clear and regular | Beautiful skin |

TABLE I-3

| Replica score | Example | | | | | Comparative Example |
|---|---|---|---|---|---|---|
|  | I-1 | I-2 | I-3 | I-4 | I-5 | I-1 |
| 1 | 0 | 0 | 0 | 0 | 0 | 2 |
| 2 | 0 | 0 | 0 | 0 | 0 | 2 |
| 3 | 0 | 0 | 1 | 2 | 1 | 5 |
| 4 | 2 | 1 | 1 | 1 | 4 | 1 |
| 5 | 8 | 9 | 8 | 7 | 5 | 0 |

The numerals in the Table indicate the number of the persons tested who exhibited the respective evaluation scores.

As shown by the results in Table I-3, the detergent compositions of the present invention (Examples I-1–I-5) exhibited a superior effective to that of the detergent composition of the Control (Comparative Example I-1).

| Example I-6 Liquid detergent for clothing | |
|---|---|
| (1) Na POE (3 mole) lauryl ether sulfate | 15.0 |
| (2) POE (15 mole) alkyl ether | 20.0 |
| (3) Distearyl dimethylammonium chloride | 2.0 |
| (4) Aprotinin | 0.5 |
| (5) Bleaching agent | q.s. |
| (6) Purified water | balance |
| Example I-7 Powder detergent for clothing | |
| (1) LAS-Na | 15.0 |
| (2) $Na_2SO_4$ | 30.0 |
| (3) 2-Phenylacetamide | 2.0 |
| (4) CMC (66%) | 1.5 |
| (5) Sodium metasilicate (anhydrous) | 20.0 |
| (6) Fluorescent brightener | 0.2 |
| (7) $Na_2CO_3$ | balance |
| Example I-8 Solid soap | |
| (1) Tallow | 20.0 |
| (2) Coconut oil | 12.0 |
| (3) Castor oil | 5.0 |
| (4) Olive oil | 3.0 |
| (5) Caustic potash | 6.0 |
| (6) Ethanol | 20.0 |
| (7) Glycerine | 5.0 |
| (8) Sucrose | 10.0 |
| (9) Cyclohexylguanidine | 3.0 |
| (10) EDTA | 0.1 |
| (11) Perfume | q.s. |
| (12) Dye | q.s. |
| (13) Purified water | balance |
| Example I-9 Liquid soap | |
| (1) Lauric acid | 3.0 |
| (2) Myristic acid | 7.0 |
| (3) Palmitic acid | 3.0 |
| (4) Oleic acid | 2.5 |
| (5) Lauroyl diethanolamide | 6.0 |
| (6) Propylene glycol | 11.0 |
| (7) Glycerine | 4.0 |
| (8) Sucrose | 5.0 |
| (9) Caustic potash | 3.0 |
| (10) EDTA | 0.1 |
| (11) p-Aminobenzimidine | 1.0 |
| (12) Perfume | q.s. |
| (13) Purified water | balance |

The respective compounds used in the following Examples were the compounds represented by the formula shown below, in which $R_1$, $R_2$, $R_3$ are respectively those shown in Table I-4.

$$R_1-NH-\underset{\overset{\|}{+NH_2}}{CH}-(CH_2)_3-\underset{\overset{|}{NH}}{CH}-CO-R_2$$
$$\phantom{R_1-NH-CH-(CH_2)_3-CH-CO-R_2}|$$
$$\phantom{R_1-NH-CH-(CH_2)_3-CH-CO-}R_3$$

TABLE I-4

| | $R_1$ | $R_2$ | $R_3$ |
|---|---|---|---|
| Compound I-1 | D-Phe—Pro | $CH_2Cl$ | 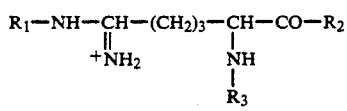 |
| Compound I-2 | Glu—Gly | $CH_2Cl$ | 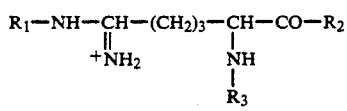 |

| Example I-10 Detergent for kitchen | |
|---|---|
| (1) Na α-Oleylsulfonate | 20.0 |
| (2) POE (15 mole) alkyl ether | 8.0 |
| (3) Laurylamide propylbetaine | 5.0 |

-continued

| | | |
|---|---|---|
| (4) Ethanol | | 1.5 |
| (5) Compound I-1 | | 3.5 |
| (6) Dye | | q.s |
| (7) Perfume | | q.s. |
| (8) Purified water | | balance |

Example I-11 Detergent for kitchen

| | | |
|---|---|---|
| (1) Monosodium N-lauroylglutamate | | 25.0 |
| (2) POE (15 mole) alkyl ether | | 5.0 |
| (3) Lauryldimethylamine oxide | | 8.0 |
| (4) Ethanol | | 1.0 |
| (5) Compound I-2 | | 7.0 |
| (6) Dye | | q.s. |
| (7) Perfume | | q.s. |
| (8) Purified water | | balance |

All of the detergent compositions of Examples I-6-I-11 were found to provide a superior skin irritation and skin irritation amelioration effect, to be harmless to the human body, and to have a strong washing power.

Actual Use Test II-1

Sixty men 30 to 50 years old and susceptible to "razor irritation" were selected as the subjects to be tested and divided into 6 groups each having 10 members. For the subjects to be tested of 5 groups, the respective Examples shown in Table II-1 were used, and for the subjects to be tested of the remaining one group, Comparative Example II-1 was used. Continuous use tests were conducted for 4 weeks, and thereafter, the state of the skin back of the hand was observed and evaluated according to the standards given in Table II-2. Each recipe was prepared according to conventional methods, to obtain an aerosol shaving foam.

TABLE II-1

| | Example | | | | | Comparative Example |
|---|---|---|---|---|---|---|
| | II-1 | II-2 | II-3 | II-4 | II-5 | II-1 |
| $C_{18}$ alkyltrimethylammonium chloride | 4.2 | 4.2 | 4.2 | 4.2 | 4.2 | 4.2 |
| Potassium myristoylglutamate | 3.5 | 3.5 | 3.5 | 3.5 | 3.5 | 3.5 |
| Lauryldimethylaminoacetic acid betaine | 8.0 | 8.0 | 8.0 | 8.0 | 8.0 | 8.0 |
| Glycerine | 3.0 | 3.0 | 3.0 | 3.0 | 3.0 | 3.0 |
| Perfume | q.s. | q.s. | q.s. | q.s. | q.s. | q.s. |
| Dye | q.s. | q.s. | q.s. | q.s. | q.s. | q.s. |
| Purified water | balance | balance | balance | balance | balance | balance |
| Propellant (L.P.G.) | 6.0 | 6.0 | 6.0 | 6.0 | 6.0 | 6.0 |
| Leupeptin | 0.3 | — | — | — | — | — |
| Tranexamic acid | — | 1.2 | — | — | — | — |
| Tosyllysyl chlormethyl ketone | — | — | 0.07 | — | — | — |
| Tosylarginine | — | — | — | 5.5 | — | — |
| Soybean trypsin inhibitor | — | — | — | — | 0.1 | — |

(The numbers in the Table show % by weight.)

TABLE II-2

Amelioration effect on razor irritation

| Evaluation | Judgement standards |
|---|---|
| Remarkably effective | Razor irritation disappeared |
| Effective | Razor irritation greatly ameliorated |
| Slightly effective | Razor irritation slightly ameliorated |
| Ineffective | Razor irritation not changed |
| Worsened | Razor irritation worsened |

TABLE II-3

| Judgement results by visual observation | Example | | | | | Comparative Example |
|---|---|---|---|---|---|---|
| | II-1 | II-2 | II-3 | II-4 | II-5 | II-1 |
| Remarkably effective | 8 | 9 | 6 | 8 | 6 | 0 |
| Effective | 2 | 1 | 3 | 1 | 2 | 1 |
| Slightly effective | 0 | 0 | 1 | 1 | 1 | 2 |
| Ineffective | 0 | 0 | 0 | 0 | 1 | 7 |
| Worsened | 0 | 0 | 0 | 0 | 0 | 0 |

The numerals in the Table show the number of the persons indicating the respective judgment results.

As shown by the results in Table II-3, the skin cleanser compositions of the present invention (Examples II-1–II-5) exhibited a superior effective to that of the skin cleanser composition of the Control (Comparative Example II-1).

Actual Use Test II-2

Thirty women 25 to 40 years old and susceptible to skin irritation were selected as the subjects to be tested and divided into three groups each having 10 members. For the subjects to be tested of two groups, the respective Examples shown in Table II-4 were used, and for the remaining one group, the Comparative Example II-2 was used, and face washing was practiced. The tests were practiced by continuous use for 4 weeks, and after completion of the test, the skin state of the cheek portion of the face was judged by the replica method. The judgment was conducted according to the standards shown in Table II-5, and the results were represented as the average of the panel of 10 members. The manner in which contaminates such as cosmetics, etc., were removed was judged by a self-evaluation by the panel members, following the standards shown in Table II-6. Each recipe was prepared according to conventional methods, to obtain a cleansing foam.

TABLE II-4

| | Example | | Comparative Example |
|---|---|---|---|
| | II-6 | II-7 | II-2 |
| Lauric acid | 8.0 | 8.0 | 8.0 |
| Myristic acid | 12.0 | 12.0 | 12.0 |
| Palmitic acid | 4.0 | 4.0 | 4.0 |
| Stearic acid | 4.0 | 4.0 | 4.0 |
| Glycerine monostearate | 1.5 | 1.5 | 1.5 |
| POE glycerylmonostearate (60 E.O.) | 2.0 | 2.0 | 2.0 |
| Glycerine | 2.5 | 2.5 | 2.5 |
| Polyoxyethylene glycol | 8.0 | 8.0 | 8.0 |

TABLE II-4-continued

|  | Example | | Comparative Example |
|---|---|---|---|
|  | II-6 | II-7 | II-2 |
| (M.W. 500) | | | |
| Sorbitol solution | 5.0 | 5.0 | 5.0 |
| Caustic potash | 5.5 | 5.5 | 5.5 |
| Purified water | balance | balance | balance |
| p-Aminobenzamidine | 0.5 | — | — |
| Tosyllysine | — | 2.0 | — |

TABLE II-5

| Score | Evaluation | Remarks |
|---|---|---|
| 1 | Disappearance of skin groove, skin rise Peeling of wide range of corneum | Irritated skin |
| 2 | Obscure skin groove, skin rise Partial peeling of corneum | ↑ |
| 3 | Skin groove, skin rise recognized, but flat | |
| 4 | Clear skin groove, skin rise | ↓ |
| 5 | Skin rise, skin groove clear and regular | Beautiful skin |

TABLE II-6

| Evaluation | Contents | |
|---|---|---|
| ⊙ | 80% | or more of the panel satisfied with good removal of contaminates. |
| o | 60% | or more of the panel satisfied with good removal of contaminates. |
| △ | 40% | or more of the panel satisfied with good removal of contaminates. |
| x | Less than 40% | or more of the panel satisfied with good removal of contaminates. |

TABLE II-7

|  | Example | | Comparative Example |
|---|---|---|---|
|  | II-6 | II-7 | II-2 |
| Replica score | 4.8 | 4.7 | 2.9 |
| Extent of contaminate removal | ⊙ | ⊙ | ⊙ |

As shown by the results given in Table II-7, the skin cleanser compositions (Examples II-6 and II-7) exhibited a superior effective to that of the skin cleanser composition of the Control (Comparative Example II-2).

|  |  | % by weight |
|---|---|---|
| Example II-8 Solid soap | | |
| (1) | Tallow | 20.0 |
| (2) | Coconut oil | 12.0 |
| (3) | Castor oil | 5.0 |
| (4) | Olive oil | 3.0 |
| (5) | Caustic potash | 6.0 |
| (6) | Ethanol | 20.0 |
| (7) | Glycerine | 5.0 |
| (8) | Sucrose | 10.0 |
| (9) | Cyclohexylguanidine | 3.0 |
| (10) | EDTA | 0.1 |
| (11) | Perfume | q.s. |
| (12) | Dye | q.s. |
| (13) | Purified water | balance |
| Example II-9 Liquid soap | | |
| (1) | Lauric acid | 3.0 |
| (2) | Myristic acid | 7.0 |
| (3) | Palmitic acid | 3.0 |
| (4) | Oleic acid | 2.5 |
| (5) | Lauroyl diethanolamide | 6.0 |
| (6) | Propylene glycol | 11.0 |
| (7) | Glycerine | 4.0 |
| (8) | Sucrose | 5.0 |
| (9) | Caustic potash | 3.0 |
| (10) | EDTA | 0.1 |
| (11) | p-Nitrophenyl-p'-guanidino-benzoic acid | 0.1 |
| (12) | Perfume | q.s. |
| (13) | Purified water | balance |

The respective compounds used in the following Examples were the compounds represented by the formula shown below, in which $R_1$, $R_2$, $R_3$ are respectively those shown in Table II-4.

$$R_1-NH-CH-(CH_2)_3-CH-CO-R_2$$
$$\overset{|}{{}^+NH_2} \qquad \overset{|}{NH}$$
$$\overset{|}{R_3}$$

TABLE II-8

| | $R_1$ | $R_2$ | $R_3$ |
|---|---|---|---|
| Compound II-1 | D-Phe—Pro | $CH_2Cl$ | 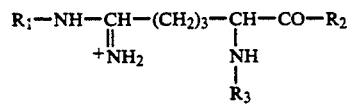 |
| Compound II-2 | Glu—Gly | $CH_2Cl$ | $SO_2$—⟨⟩—$CH_3$ |
| Compound II-3 | Ile—Glu—Gly | $CH_2Cl$ | $SO_2$—⟨⟩—$CH_3$ |
| Compound II-4 | Pro—Phe | $CH_2Cl$ | $SO_2$—⟨⟩—$CH_3$ |

|  |  | % by weight |
|---|---|---|
| Example II-10 Cleaning cream | | |
| (1) | Solid paraffin | 3.5 |
| (2) | Microcrystalline wax | 8.0 |
| (3) | Beeswax | 5.0 |
| (4) | Petroplatum | 1.0 |
| (5) | Fluid paraffin | 43.0 |
| (6) | Glycerine monooleate | 4.0 |
| (7) | POE (20 mole) monooleate | 0.5 |
| (8) | Compounds II-1 | 5.0 |
| (9) | Perfume | q.s. |
| (10) | Purified water | balance |
| Example II-11 Emulsified type cleansing lotion | | |
| (1) | Stearic acid | 3.0 |
| (2) | Cetyl alcohol | 1.0 |
| (3) | Petrolatum | 4.5 |
| (4) | Fluid paraffin | 11.0 |
| (5) | POE (20 mole) oleyl alcohol ether | 1.5 |
| (6) | POE (5 mole) sorbitane monolauric acid ether | 1.0 |
| (7) | Triethanolamine | 1.0 |
| (8) | Propylene glycol | 6.0 |
| (9) | Compound II-2 | 1.0 |
| (10) | Perfume | q.s. |
| (11) | Purified water | balance |
| Example II-12 Non-emulsified type cleansing lotion | | |
| (1) | Propylene glycol | 10.0 |
| (2) | Dipropylene glycol | 6.0 |
| (3) | N,N-dimethyl-lauryl-N-carboxymethyl-ammonium-betaine | 2.0 |
| (4) | POE (20 mole) sorbitane | 3.0 |

| | | % by weight |
|---|---|---|
| | monolauric acid ether | |
| (5) | Ethyl alcohol | 10.0 |
| (6) | Compound II-3 | 5.0 |
| (7) | Perfume | q.s. |
| (8) | Purified water | balance |

Example II-13 Aerosol shaving foam (Filling recipe)

| (1) | Stearic acid | 5.5 |
|---|---|---|
| (2) | Purified coconut fatty acids | 1.5 |
| (3) | Glyceryl monostearate | 5.0 |
| (4) | Glycerine | 10.0 |
| (5) | Triethanolamine | 4.0 |
| (6) | Compound II-4 | 0.05 |
| (7) | Perfume | q.s. |
| (8) | Purified water | balance |

(Filling recipe)

| (1) | Stock solution | 94.0 |
|---|---|---|
| (2) | LPG | 6.0 |

Examples II-8 to II-13 were found to perfectly harmless and to have a strong washing power.

We claim:

1. In a washing composition containing at least one surfactant but not containing protease, the improvement which comprises incorporating said composition 0.0001% to 20% by weight, based on the total weight of the composition, of at least one compound selected from the group consisting of (a) leupeptin and the derivatives thereof having the formula:

$$R_1-R_2-R_3-NH-\underset{CHO}{CH}-(CH_2)_3-NH-\underset{+NH_2}{\overset{\parallel}{C}H}-NH_2$$

wherein:
$R_1 = CH_3CO, CH_3CH_2CO$
$R_2 = $ L-Leu, L-Ile, L-Val
$R_3 = $ L-Leu, L-Ile, L-Val
Leu = leucine,
Ile = isoleucine, and
Val = valine, and (b) tranexamic acid, p-aminomethylbenzoic acid, 4-aminomethylbicyclo(2,2,2)-octane-1-carboxylic acid, 5-[trans-4(aminomethyl)cyclohexyl]tetrazole, 3-[trans-4(aminomethyl)cyclohexyl]-2-oxopropionate, trans-4(aminomethyl)cyclohexyl glyoxal monohydrate, and trans-4(aminomethyl)cyclohexane hydroxamic acid, and substances represented by the following formula:

$$NH_2(CH_2)_nCOOH.$$

wherein $n = 1-8$.

2. A washing composition as claimed in claim 1, wherein said compound is leupeptin.

3. A washing composition as claimed in claim 1, wherein said compound is tranexamic acid.

* * * * *